(12) United States Patent
Davidson et al.

(10) Patent No.: US 8,063,103 B2
(45) Date of Patent: Nov. 22, 2011

(54) POLYMORPHS OF ACYL SULFONAMIDES

(75) Inventors: James Prentice Davidson, Mountain View, CA (US); Fei Pang, Sunnyvale, CA (US); Margaret Wong, Redwood City, CA (US); Michael Martin, Palo Alto, CA (US)

(73) Assignee: Roche Palo Alto LLC, South San Francisco, CA (US)

( * ) Notice: Subject to any disclaimer, the term of this patent is extended or adjusted under 35 U.S.C. 154(b) by 164 days.

(21) Appl. No.: 12/556,235

(22) Filed: Sep. 9, 2009

(65) Prior Publication Data

US 2010/0063154 A1    Mar. 11, 2010

Related U.S. Application Data

(60) Provisional application No. 61/095,364, filed on Sep. 9, 2008.

(51) Int. Cl.
   *C07C 311/51* (2006.01)
   *A61K 31/277* (2006.01)
(52) U.S. Cl. ........... 514/522; 514/603; 558/414; 564/86
(58) Field of Classification Search .................. 514/603, 514/522; 558/414; 564/86
   See application file for complete search history.

(56) References Cited

U.S. PATENT DOCUMENTS

| | | | |
|---|---|---|---|
| 7,166,738 B2 | 1/2007 | Dunn et al. | |
| 7,625,949 B2 | 12/2009 | Dunn et al. | |
| 2005/0239881 A1 | 10/2005 | Dunn et al. | |
| 2010/0041648 A1 | 2/2010 | Dunn et al. | |

OTHER PUBLICATIONS

Giron, D. J. Therm. Anal. Cal. 2001, 64, pp. 37-60.*
Giron, D. J. Therm. Anal. Cal. 2002, 68, pp. 335-357.*
B. Rodriquez-Spong et al. Advanced Drug Delivery Reviews, 2004, 56, pp. 241-274.*
Souillac, et al., Characterization of Delivery Systems, Differential Scanning Calorimetry, pp. 217-218 (in Encyclopedia of Controlled Drug Delivery, 1999, John Wiley & Sons, pp. 212-227.*
Graham, B.S., "Clinical trials of HIV vaccines." HIV Molecular Immunology Database 2000. Edited by: Korber BT, Brander C, Haynes BF, Koup R, Kuiken C, Moore JP, Walker BD, and Watkins D. Published by: Theoretical Biology and Biophysics Group, Los Alamos National Laboratory, Los Alamos, NM. pp. I-20-38, 2000.*

* cited by examiner

*Primary Examiner* — Joseph Kosack
*Assistant Examiner* — Matthew Coughlin
(74) *Attorney, Agent, or Firm* — Brian L. Buckwalter

(57) ABSTRACT

The application discloses novel polymorphic crystalline forms of 2-[4-Bromo-3-(3-chloro-5-cyano-phenoxy)-2-fluoro-phenyl]-N-(2-chloro-4-propionylsulfamoyl-phenyl)-acetamide, sodium salt (Ib)

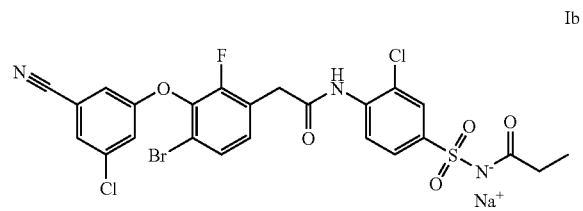

with improved stability and physical properties which facilitate manufacturing, handling and formulating for treatment or prophylaxis of HIV mediated diseases, AIDS or ARC, in monotherapy or in combination therapy.

14 Claims, 11 Drawing Sheets

X-ray powder diffraction pattern of the Form I polymorphic form of Ib.

Figure 1. X-ray powder diffraction pattern of the Form I polymorphic form of Ib.
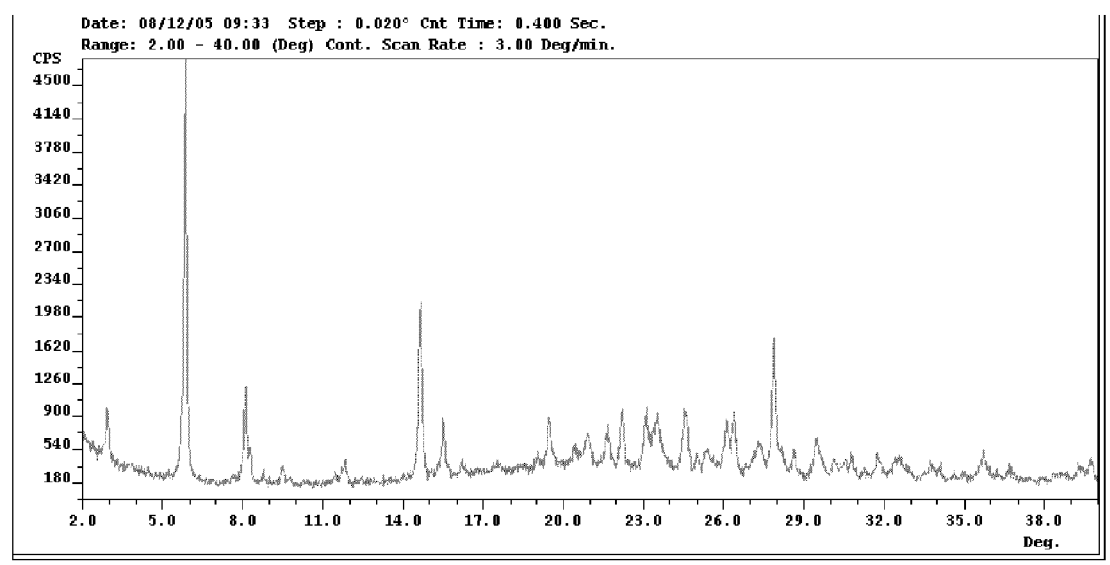

Figure 2a. X-ray powder diffraction pattern of the Form II polymorphic form of Ib.
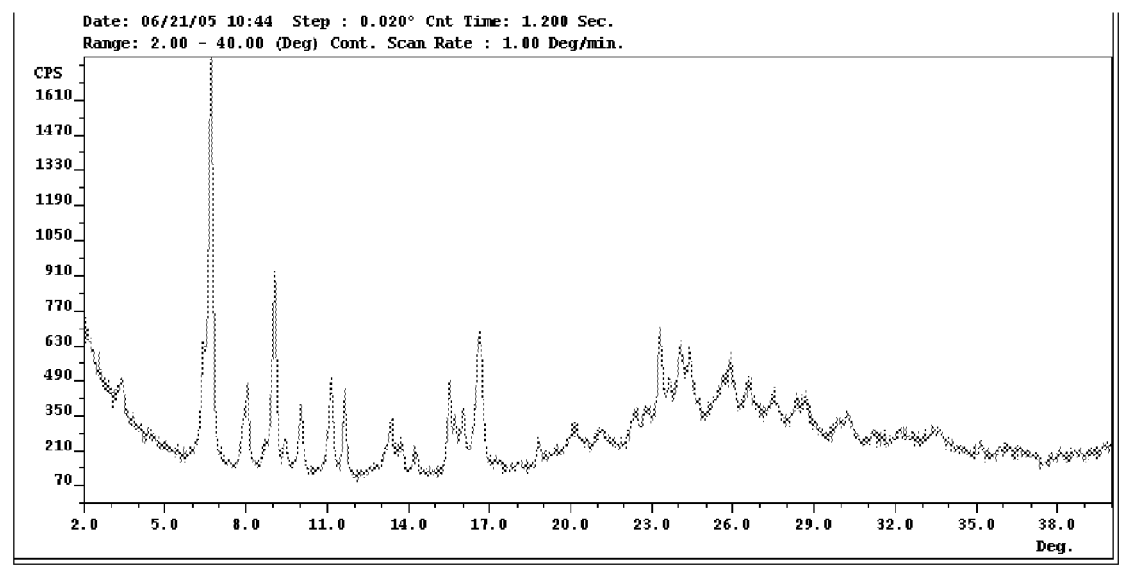
Figure 2b. Differential scanning calorimetry (DSC) trace and the thermal gravimetic analysis (TGA) trace of the Form II polymorphic form of Ib.
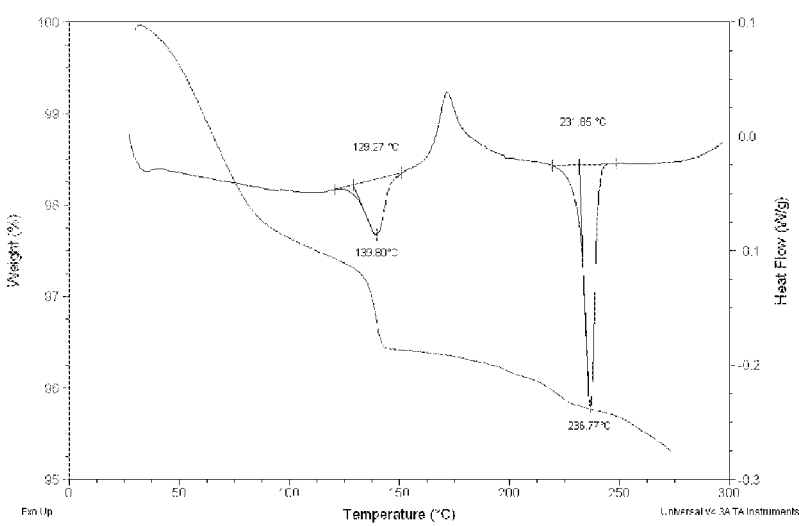

Figure 3a. X-ray powder diffraction pattern of the Form III polymorphic form of Ib.
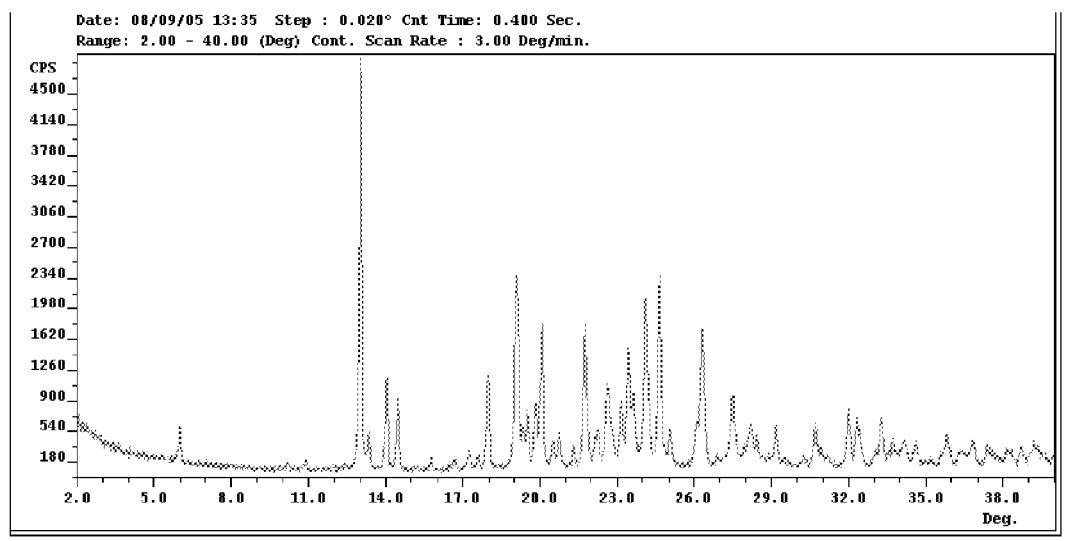
Figure 3b. Differential scanning calorimetry (DSC) trace and the thermal gravimetic analysis (TGA) trace of the Form III polymorphic form of Ib.
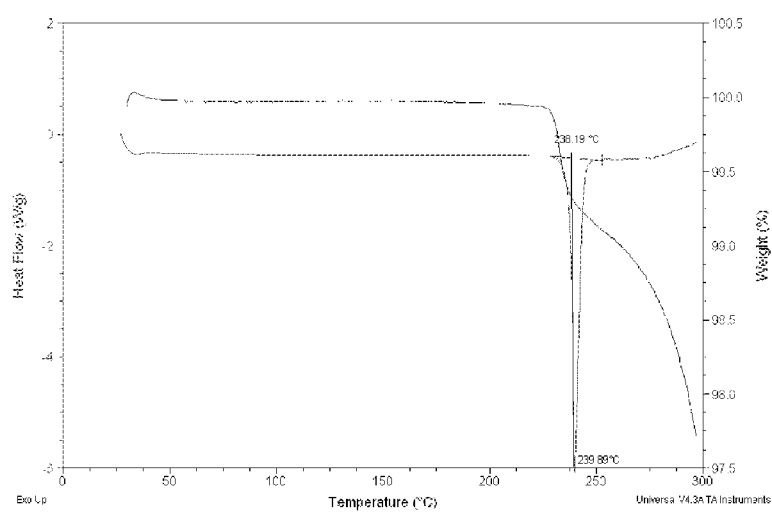

Figure 4. X-ray powder diffraction pattern of the Form IV polymorphic form of Ib.
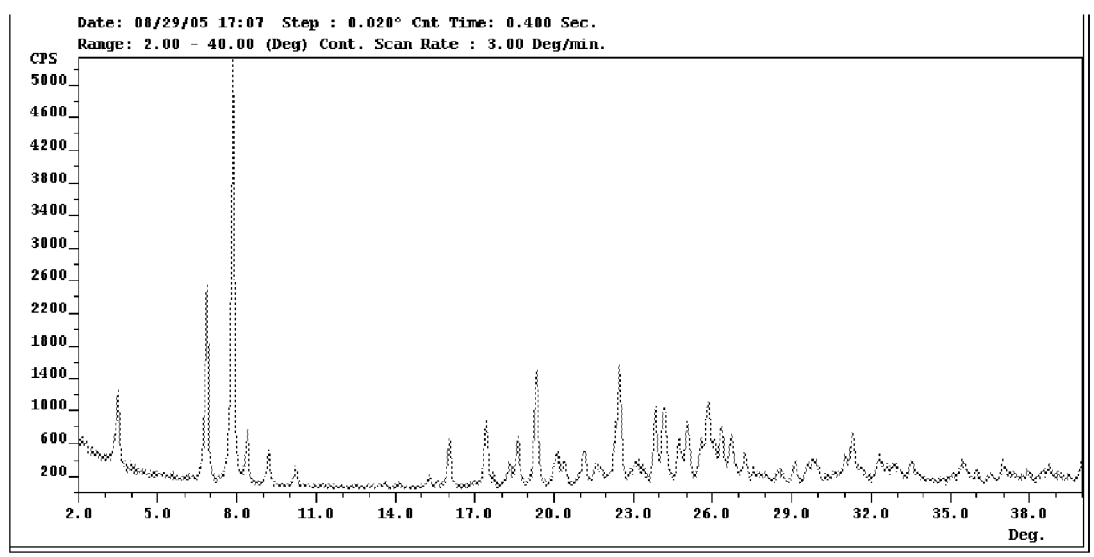

Figure 5. X-ray powder diffraction pattern of the Form V polymorphic form of Ib.
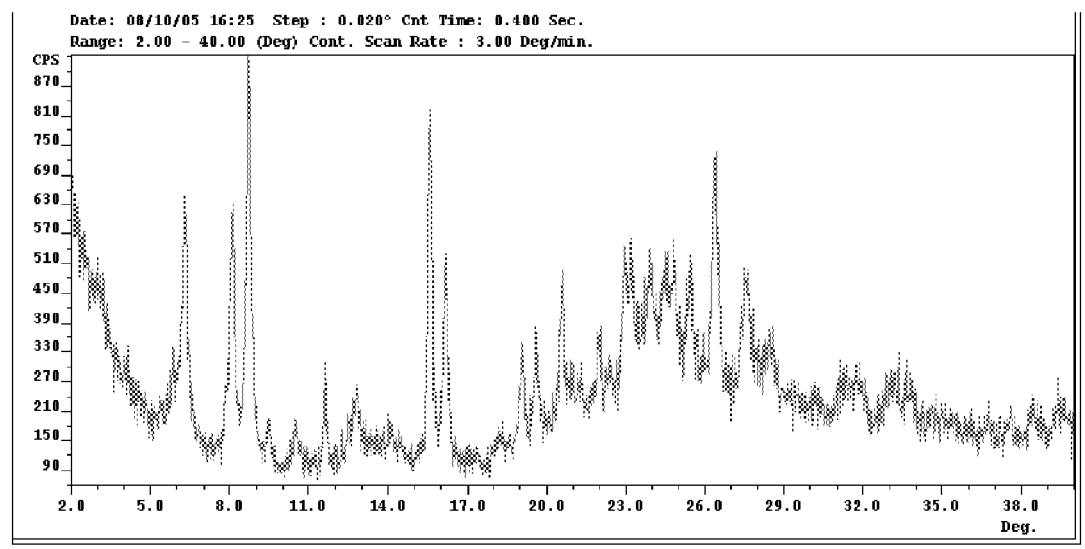

Figure 6. X-ray powder diffraction pattern of the Form VI polymorphic form of Ib.
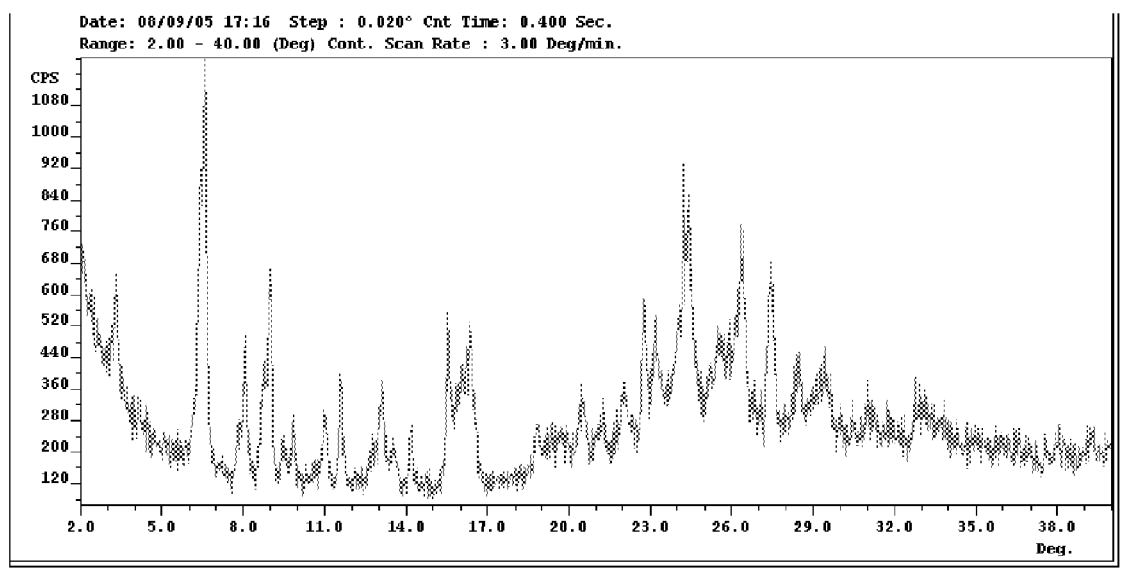

Figure 7. X-ray powder diffraction pattern of the Form VII polymorphic form of Ib.
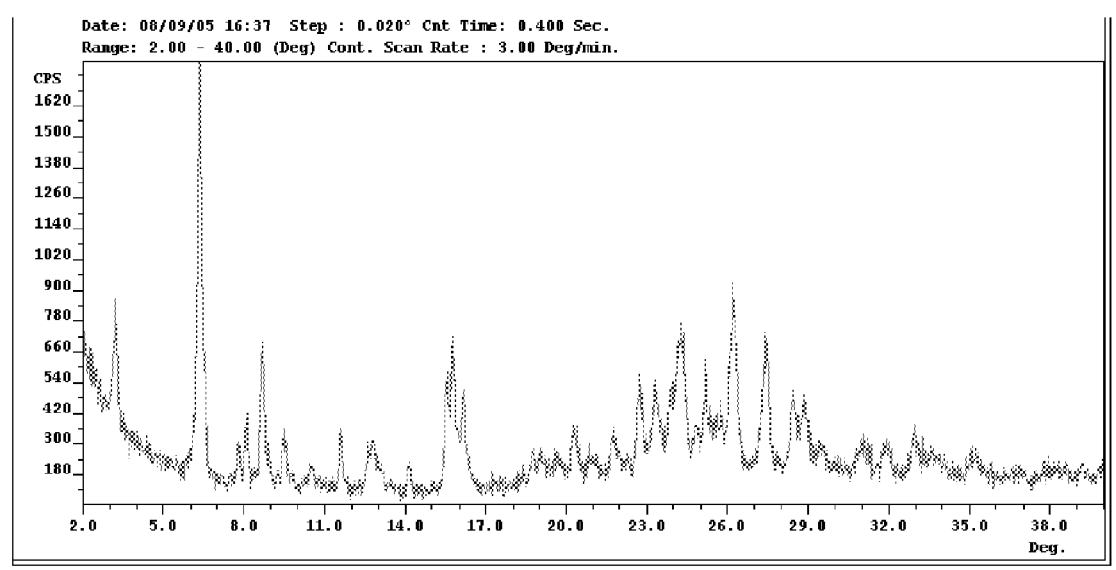

Figure 8a. X-ray powder diffraction pattern of the Form VIII polymorphic form of Ib. The diffraction data for Form VIII tabulated in Table A in the specification
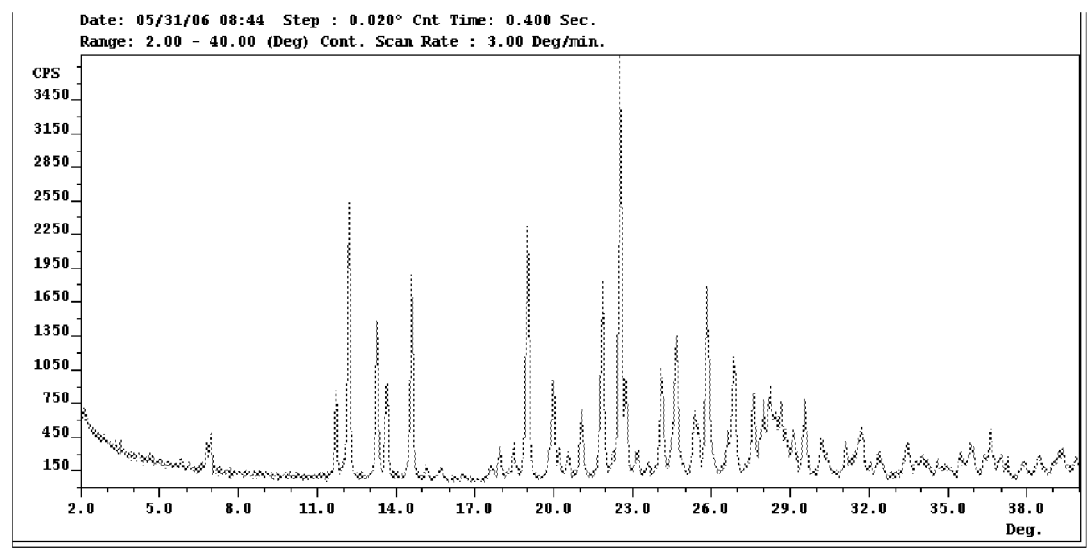
Figure 8b. Differential scanning calorimetry (DSC) trace and the thermal gravimetic analysis (TGA) trace of the Form VIII polymorphic form of Ib.
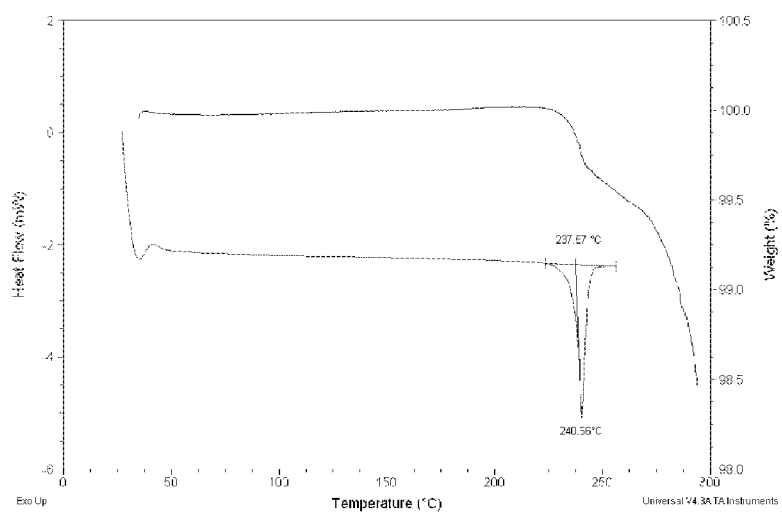

Figure 9a. X-ray powder diffraction of the Form IX polymorphic form of Ib.
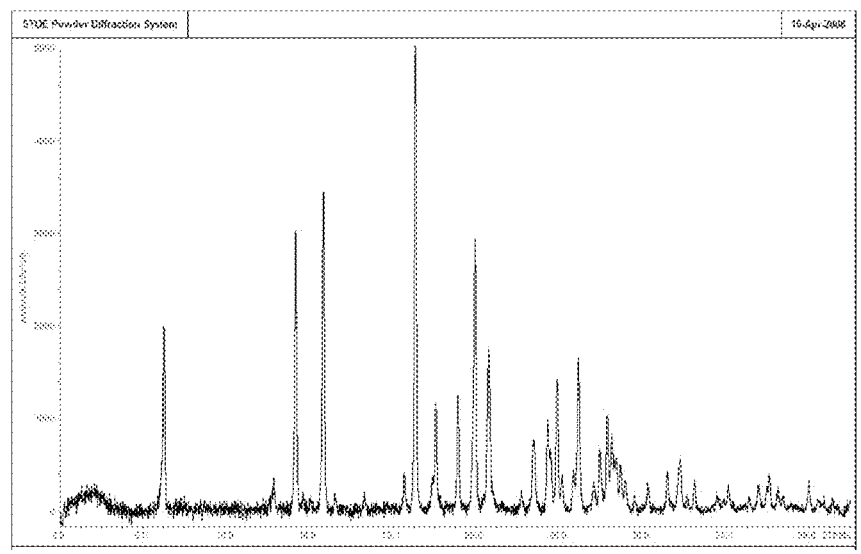
Figure 9b. Differential scanning calorimetry (DSC) trace and the thermal gravimetic analysis (TGA) trace of the Form IX polymorphic form of Ib.
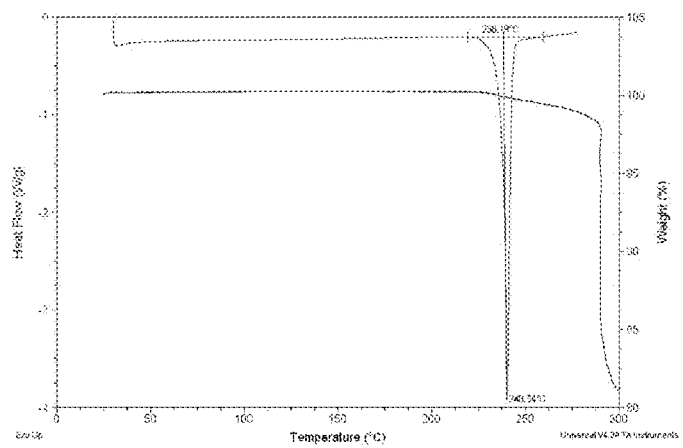

Figure 10. X-ray powder diffraction of the amorphous state of Ib.
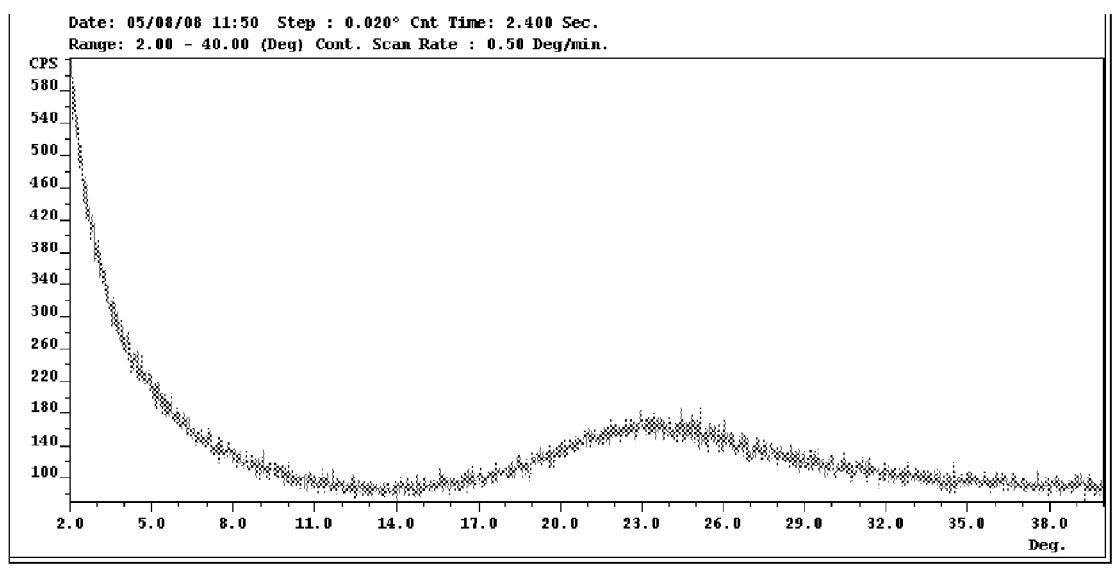

Figure 11. The interconversion scheme for crystalline polymorph Forms I-IX and amorphous state of Ib.
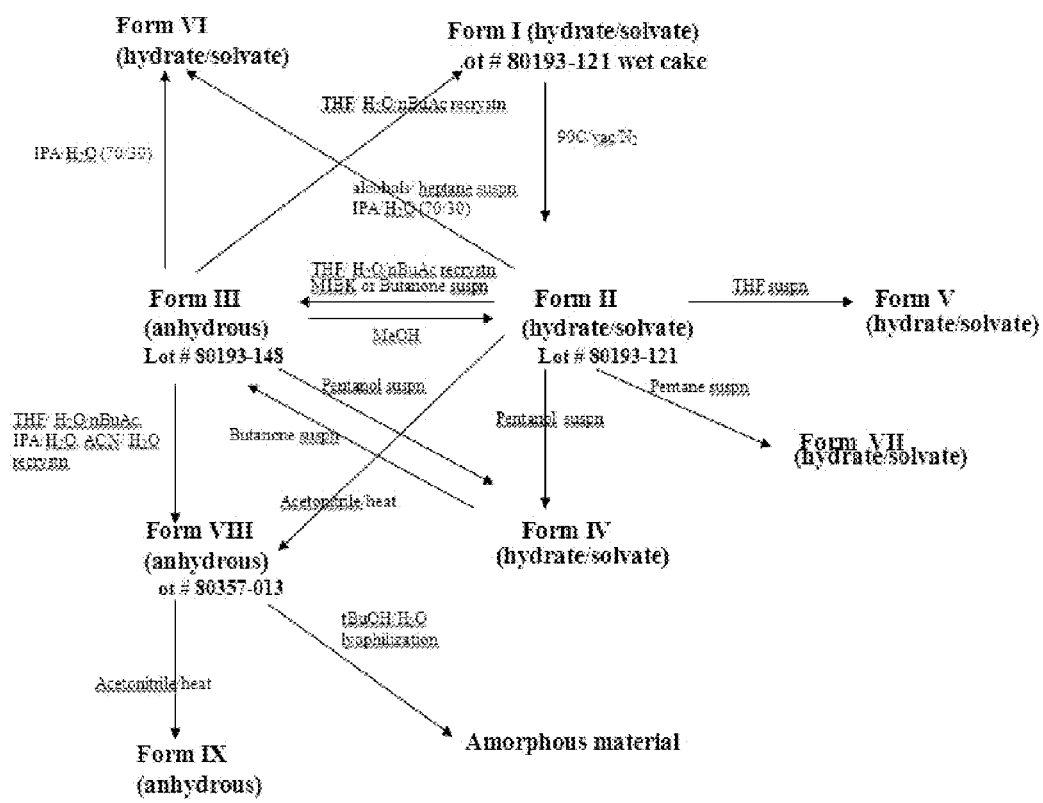

POLYMORPHS OF ACYL SULFONAMIDES

CROSS-REFERENCE TO RELATED APPLICATIONS

This application is entitled to the benefit of U.S. provisional patent application Ser. No. 61/095,364 filed on Sep. 9, 2008, the disclosure of which is incorporated herein by reference.

FIELD OF THE INVENTION

The invention relates to novel polymorphic crystalline forms of 2-[4-Bromo-3-(3-chloro-5-cyano-phenoxy)-2-fluoro-phenyl]-N-(2-chloro-4-propionylsulfamoyl-phenyl)-acetamide sodium salt, with improved stability and physical properties which facilitate manufacturing, handling and formulating for treatment or prophylaxis of HIV mediated diseases, AIDS or ARC, in monotherapy or in combination therapy.

BACKGROUND OF THE INVENTION

The human immunodeficiency virus HIV is the causative agent of acquired immunodeficiency syndrome (AIDS), a disease characterized by the destruction of the immune system, particularly of the $CD4^+$ T-cell, with attendant susceptibility to opportunistic infections. HIV infection is also associated with a precursor AIDs-related complex (ARC), a syndrome characterized by symptoms such as persistent generalized lymphadenopathy, fever and weight loss.

In common with other retroviruses, the HIV genome encodes protein precursors known as gag and gag-pol which are processed by the viral protease to afford the protease, reverse transcriptase (RT), endonuclease/integrase and mature structural proteins of the virus core. Interruption of this processing prevents the production of normally infectious virus. Considerable efforts have been directed towards the control of HIV by inhibition of virally encoded enzymes.

Currently available chemotherapy targets two crucial viral enzymes: HIV protease and HIV reverse transcriptase. (J. S. G. Montaner et al. *Antiretroviral therapy: 'the state of the art'*, Biomed & Pharmacother. 1999 53:63-72; R. W. Shafer and D. A. Vuitton, *Highly active retroviral therapy (HAART) for the treatment of infection with human immunodeficiency virus type*, Biomed. & Pharmacother. 1999 53 :73-86; E. De Clercq, *New Developments in Anti-HIV Chemotherap.* Curr. Med. Chem. 2001 8:1543-1572). Two general classes of RTI inhibitors have been identified: nucleoside reverse transcriptase inhibitors (NRTI) and non-nucleoside reverse transcriptase inhibitors.

NRTIs typically are 2',3'-dideoxynucleoside (ddN) analogs which must be phosphorylated prior to interacting with viral RT. The corresponding triphosphates function as competitive inhibitors or alternative substrates for viral RT. After incorporation into nucleic acids the nucleoside analogs terminate the chain elongation process. HIV reverse transcriptase has DNA editing capabilities which enable resistant strains to overcome the blockade by cleaving the nucleoside analog and continuing the elongation. Currently clinically used NRTIs include zidovudine (AZT), didanosine (ddI), zalcitabine (ddC), stavudine (d4T), lamivudine (3TC) and tenofovir (PMPA).

NNRTIs were first discovered in 1989. NNRTI are allosteric inhibitors which bind reversibly at a nonsubstrate-binding site on the HIV reverse transcriptase thereby altering the shape of the active site or blocking polymerase activity (R. W. Buckheit, Jr., *Non-nucleoside reverse transcriptase inhibitors: perspectives for novel therapeutic compounds and strategies for treatment of HIV infection*, Expert Opin. Investig. Drugs 200110(8)1423-1442; E. De Clercq *The role of non-nucleoside reverse transcriptase inhibitors (NNRTIs) in the therapy of HIV infection*, Antiviral Res. 1998 38:153-179; E. De Clercq *New Developments in Anti-HIV Chemotherapy*, Current medicinal Chem. 2001 8(13):1543-1572; G. Moyle, *The Emerging Roles of Non-Nucleoside Reverse Transcriptase Inhibitors in Antiviral Therapy*, Drugs 2001 61 (1): 19-26). Although over thirty structural classes of NNRTIs have been identified in the laboratory, only three compounds have been approved for HIV therapy: efavirenz, nevirapine and delavirdine.

Initially viewed as a promising class of compounds, in vitro and in vivo studies quickly revealed the NNRTIs presented a low barrier to the emergence of drug resistant HIV strains and class-specific toxicity. Drug resistance frequently develops with only a single point mutation in the RT. While combination therapy with NRTIs, PIs and NNRTIs has, in many cases, dramatically lowered viral loads and slowed disease progression, significant therapeutic problems remain. (R. M. Gulick, Eur. Soc. Clin. Microbiol. and Inf. Dis. 2003 9(3):186-193) The cocktails are not effective in all patients, potentially severe adverse reactions often occur and the rapidly reproducing HIV virus has proven adroit at creating mutant drug-resistant variants of wild type protease and reverse transcriptase. There remains a need for safer drugs with activity against wild type and commonly occurring resistant strains of HIV.

2-[4-Bromo-3-(3-chloro-5-cyano-phenoxy)-2-fluoro-phenyl]-N-(2-chloro-4-propionylsulfamoyl-phenyl)-acetamide, sodium salt, the compound of formula Ib

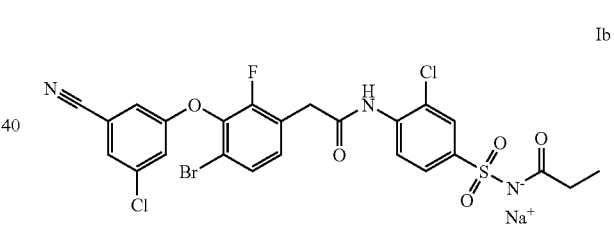

Ib was disclosed, as well as its method of preparation, and its activity as an inhibitor of HIV Reverse Transcriptase in U.S. Pat. No. 7,166,738, which is herein incorporated by reference in its entirety.

Salts of acidic and basic compounds can alter or improve the physical properties of a parent compound. These salt forming agents, however, must be identified empirically by the pharmaceutical chemist since there is no reliable method to predict the influence of a salt species on the behavior of a parent compound in dosage forms.

Polymorphism is the ability of any element or compound to crystallize as more than one distinct crystalline species. Different polymorphic forms of salts are frequently encountered among pharmaceutically useful compounds. Physical properties including solubility, melting point, density, hardness, crystalline shape and stability can be quite different for different polymorphic forms of the same chemical compound.

Polymorphic forms are characterized by scattering techniques, e.g., x-ray diffraction powder pattern, by spectroscopic methods, e.g., infa-red, 13C nuclear magnetic resonance spectroscopy and by thermal techniques, e.g, differential scanning calorimetry or differential thermal analysis. Polymorphs are best characterized by the X-ray powder diffraction pattern determined in accordance with procedures which are known in the art. For a discussion of these techniques see J. Haleblian, J. Pharm. Sci. 1975 64:1269-1288, and J. Haleblain and W. McCrone, J. Pharm. Sci. 1969 58:911-929. Although the intensities of peaks in the x-ray powder diffraction patterns of different batches of a polymorph may vary slightly, the peaks and their relative peak positions are characteristic for a specific polymorphic form.

The problem which must be solved is to identify a suitable salt and/or polymorph which (i) possesses adequate physical and chemical stability during the manufacturing process, (ii) is efficiently prepared, purified and recovered, (ii) provides acceptable solubility in pharmaceutically acceptable solvents, (iii) is amenable to manipulation (e.g. flowability and particle size) and formulation with negligible decomposition or change of the physical and chemical characteristics of the compound, (iv) exhibits acceptable physical and chemical stability in the formulation. In addition, salts which contribute minimally to the molar weight so that the resulting material comprises a high molar percent of the active ingredient are highly desirable since the quantity of material which must be formulated and administered to produce a therapeutically effective dose is minimized. These oft conflicting requirements make identification suitable salts a challenging and important problem which must be solved by the skilled pharmaceutical scientist before drug development can proceed in earnest.

SUMMARY OF THE INVENTION

This invention relates to 9 polymorphic crystalline forms, I-IX, of 2-[4-Bromo-3-(3-chloro-5-cyano-phenoxy)-2-fluoro-phenyl]-N-(2-chloro-4-propionylsulfamoyl-phenyl)-acetamide, sodium salt (Ib)

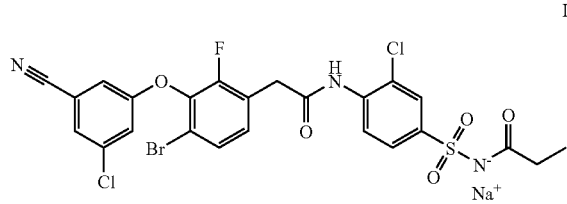

methods to prepare polymorphic crystalline forms I-IX, pharmaceutical compositions containing the polymorphic forms I-IX, and methods to treat diseases related to HIV using polymorphic forms of I-IX.

The application provides a crystalline form of a compound according to formula Ib.

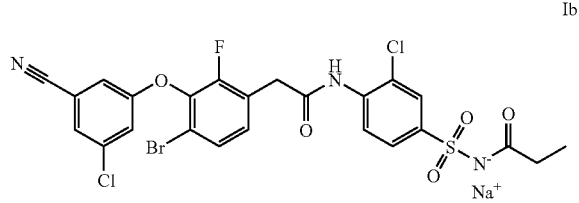

The application further provides a process for preparing a polymorph of the crystalline form of the above compound according to formula Ib, comprising crystallizing the compound (Ib) from THF, water, and nBuAc.

The application further provides a polymorphic crystalline form of a compound according to formula Ib prepared in accordance with the above process.

The application further provides a polymorphic crystalline form (Form I) of a compound according to formula Ib with an x-ray powder diffraction trace having a D-spacing essentially as shown:

| D-space | $I/I_o \times 100$ |
|---------|---------------------|
| 15.1    | 100.0               |
| 10.9    | 21.9                |
| 6.0     | 39.5                |
| 3.2     | 30.0                |

The application further provides a polymorphic crystalline form (Form II) of a compound according to formula Ib with an x-ray powder diffraction trace having a D-spacing essentially as shown:

| D-space | $I/I_o \times 100$ |
|---------|---------------------|
| 13.2    | 100.0               |
| 9.8     | 44.0                |
| 7.9     | 20.9                |
| 7.6     | 17.3                |
| 5.3     | 30.5                |

The application further provides a polymorphic crystalline form (Form III) of a compound according to formula Ib with an x-ray powder diffraction trace having a D-spacing essentially as shown:

| D-space | $I/I_o \times 100$ |
|---------|---------------------|
| 6.8     | 100.0               |
| 4.6     | 44.0                |
| 4.4     | 31.7                |
| 4.1     | 31.5                |
| 3.7     | 36.9                |
| 3.6     | 42.7                |
| 3.4     | 32.3                |

The application further provides a polymorphic crystalline form (Form IV) of a compound according to formula Ib with an x-ray powder diffraction trace having a D-spacing essentially as shown:

| D-space | $I/I_o \times 100$ |
|---------|---------------------|
| 12.9    | 43.0                |
| 11.3    | 100.0               |
| 4.6     | 25.6                |
| 4.0     | 23.7                |

The application further provides a polymorphic crystalline form (Form V) of a compound according to formula Ib with an x-ray powder diffraction trace having a D-spacing essentially as shown:

| D-space | I/I$_o$ × 100 |
| --- | --- |
| 13.9 | 56.2 |
| 10.8 | 58.2 |
| 10.1 | 100.0 |
| 5.7 | 87.7 |
| 5.5 | 45.4 |
| 3.4 | 54.9 |
| 3.2 | 27.5 |

The application further provides a polymorphic crystalline form (Form VI) of a compound according to formula Ib with an x-ray powder diffraction trace having a D-spacing essentially as shown:

| D-space | I/I$_o$ × 100 |
| --- | --- |
| 13.4 | 100.0 |
| 10.9 | 38.4 |
| 9.8 | 48.4 |
| 5.7 | 40.1 |
| 5.4 | 37.6 |
| 3.6 | 41.8 |
| 3.4 | 38.8 |
| 3.2 | 35.4 |

The application further provides a polymorphic crystalline form (Form VII) of a compound according to formula Ib with an x-ray powder diffraction trace having a D-spacing essentially as shown:

| D-space | I/I$_o$ × 100 |
| --- | --- |
| 13.9 | 100.0 |
| 10.2 | 33.4 |
| 5.6 | 33.0 |
| 3.7 | 26.2 |
| 3.4 | 36.7 |
| 3.3 | 27.9 |

The application further provides a polymorphic crystalline form (Form VIII) of a compound according to formula Ib with an x-ray powder diffraction trace having a D-spacing essentially as shown:

| D-space | I/I$_o$ × 100 |
| --- | --- |
| 7.2 | 65.6 |
| 6.7 | 34.3 |
| 6.1 | 45.3 |
| 4.7 | 53.9 |
| 4.1 | 45.2 |
| 3.9 | 100.0 |
| 3.4 | 43.4 |

The application further provides a polymorphic crystalline form (Form IX) of a compound according to formula Ib with an x-ray powder diffraction trace having a D-spacing essentially as shown:

| D-space | I/I$_o$ × 100 |
| --- | --- |
| 12.6 | 39.1 |
| 6.6 | 58.9 |
| 6.0 | 68.9 |
| 4.6 | 100.0 |
| 4.0 | 57.7 |
| 3.9 | 35.4 |
| 3.3 | 32.4 |

The application further provides a process for preparing the polymorphic crystalline form (Form III) comprising crystallizing the compound (Ib) from THF/water/n-butanol/n-butyl acetate, THF/nBuAc, butanone, or methyl isobutyl ketone.

The application further provides a process for preparing the polymorphic crystalline form (Form VIII) comprising crystallizing the compound (Ib) from THF/water/butyl acetate, acetonitrile, acetonitrile/water, or isopropanol/water.

The application further provides a process for preparing the polymorphic crystalline form (Form IX) comprising crystallizing the compound (Ib) from acetonitrile.

The application further provides a method of treating a disease associated with HIV comprising administering to a patient in need thereof, a therapeutically effective amount of any one of polymorph Forms I-IX of compound Ib.

The application further provides the above method, further comprising administering an immune system modulator or an antiviral compound.

The application further provides a pharmaceutical composition comprising any one of polymorph Forms I-IX of compound Ib in admixture with at least one pharmaceutically acceptable carrier, diluent or excipient.

The application further provides a method of treating a disease associated with HIV comprising administering to a patient in need thereof, a therapeutically effective amount of the amorphous state of compound Ib.

The application further provides the above method, further comprising administering an immune system modulator or an antiviral compound.

The application further provides a pharmaceutical composition comprising of the amorphous state of compound Ib in admixture with at least one pharmaceutically acceptable carrier, diluent or excipient.

BRIEF DESCRIPTION OF THE FIGURES

The numerous objects and advantages of the present invention can be directly understood by those skilled in the art by reference to the accompanying figures in which:

FIG. 1 shows the x-ray powder diffraction pattern of the Form I polymorphic form of Ib.

FIG. 2a shows the x-ray powder diffraction pattern of the Form II polymorphic form of Ib.

FIG. 2b shows the differential scanning calorimetry (DSC) trace and the thermal gravimetic analysis (TGA) trace of the Form II polymorphic form of Ib.

FIG. 3a shows the x-ray powder diffraction pattern of the Form III polymorphic form of Ib.

FIG. 3b shows the differential scanning calorimetry (DSC) trace and the thermal gravimetic analysis (TGA) trace of the Form III polymorphic form of Ib.

FIG. 4 shows the x-ray powder diffraction pattern of the Form IV polymorphic form of Ib.

FIG. 5 shows the x-ray powder diffraction pattern of the Form V polymorphic form of Ib.

FIG. 6 shows the x-ray powder diffraction pattern of the Form VI polymorphic form of Ib.

FIG. 7 shows the x-ray powder diffraction pattern of the Form VII polymorphic form of Ib.

FIG. 8*a* shows the x-ray powder diffraction pattern of the Form VIII polymorphic form of Ib. The diffraction data for Form VIII tabulated in Table 8 in the specification FIG. 8*b* shows the differential scanning calorimetry (DSC) trace and the thermal gravimetic analysis (TGA) trace of the Form VIII polymorphic form of Ib.

FIG. 9*a* shows the x-ray powder diffraction of the Form IX polymorphic form of Ib.

FIG. 9*b* shows the differential scanning calorimetry (DSC) trace and the thermal gravimetic analysis (TGA) trace of the Form IX polymorphic form of Ib.

FIG. 10. X-ray powder diffraction of the amorphous state of Ib.

FIG. 11 shows the interconversion scheme of crystalline polymorph forms I-IX and amorphous state of Ib.

DETAILED DESCRIPTION OF THE INVENTION

New crystalline forms of 2-[4-Bromo-3-(3-chloro-5-cyano-phenoxy)-2-fluoro-phenyl]-N-(2-chloro-4-propionyl-sulfamoyl-phenyl)-acetamide sodium salt (Ib) have been identified with superior chemical and physical properties which facilitate manufacturing and formulation of the compound. In an embodiment of the present invention there is provided a crystalline form of a compound according to formula Ib.

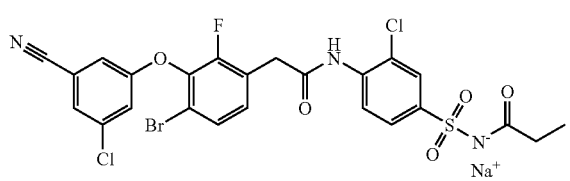

Ib

In another embodiment of the present invention there is provided

Preparation and Properties

The powder x-ray diffraction pattern of Form I is shown in FIG. 1 and values are tabulated in Table I.

TABLE I

| D-space | $I/I_o \times 100$ |
| --- | --- |
| 15.1 | 100.0 |
| 10.9 | 21.9 |
| 7.5 | 5.3 |
| 6.0 | 39.5 |
| 5.7 | 11.9 |
| 4.6 | 10.6 |
| 4.2 | 6.5 |
| 4.1 | 9.6 |
| 4.0 | 13.4 |
| 3.8 | 12.7 |
| 3.8 | 10.6 |
| 3.6 | 13.0 |
| 3.4 | 10.3 |
| 3.4 | 12.1 |
| 3.3 | 5.5 |
| 3.2 | 30.0 |
| 3.2 | 4.8 |
| 3.1 | 5.2 |
| 3.0 | 6.9 |
| 2.9 | 4.8 |
| 2.8 | 5.0 |
| 2.5 | 6.3 |

The powder x-ray diffraction pattern of Form II is shown in FIG. 2*a* and values are tabulated in Table II.

TABLE II

| D-space | $I/I_o \times 100$ |
| --- | --- |
| 13.7 | 27.4 |
| 13.2 | 100.0 |
| 11.0 | 18.1 |
| 9.8 | 44.0 |
| 9.4 | 5.3 |
| 8.8 | 14.1 |
| 7.9 | 20.9 |
| 7.6 | 17.3 |
| 6.6 | 11.9 |
| 6.5 | 5.1 |
| 6.2 | 5.1 |
| 5.7 | 17.9 |
| 5.6 | 9.5 |
| 5.5 | 11.8 |
| 5.3 | 30.5 |
| 4.4 | 4.8 |
| 4.4 | 5.2 |
| 4.0 | 3.8 |
| 3.8 | 18.2 |
| 3.8 | 6.7 |
| 3.7 | 15.4 |
| 3.6 | 13.5 |
| 3.5 | 8.1 |
| 3.5 | 8.8 |
| 3.4 | 13.4 |
| 3.3 | 6.8 |
| 3.2 | 7.4 |
| 3.2 | 4.0 |
| 3.1 | 6.1 |
| 3.1 | 7.2 |
| 3.0 | 4.2 |
| 3.0 | 6.3 |
| 2.7 | 4.3 |
| 2.7 | 3.7 |

The powder x-ray diffraction pattern of Form III is shown in FIG. 3*a* and values are tabulated in Table III.

TABLE III

| D-space | $I/I_o \times 100$ |
| --- | --- |
| 14.7 | 8.8 |
| 6.8 | 100.0 |
| 6.6 | 7.6 |
| 6.3 | 21.2 |
| 6.1 | 16.5 |
| 4.9 | 21.7 |
| 4.6 | 44.0 |
| 4.6 | 6.9 |
| 4.5 | 11.6 |
| 4.5 | 13.4 |
| 4.4 | 31.7 |
| 4.3 | 7.5 |
| 4.1 | 31.5 |
| 4.0 | 5.7 |
| 3.9 | 16.6 |
| 3.8 | 11.1 |
| 3.8 | 25.0 |
| 3.8 | 13.6 |
| 3.7 | 36.9 |
| 3.6 | 42.7 |
| 3.6 | 7.6 |
| 3.4 | 32.3 |
| 3.2 | 14.8 |
| 3.2 | 7.7 |
| 3.1 | 8.2 |
| 2.9 | 9.1 |
| 2.8 | 11.4 |
| 2.8 | 9.6 |
| 2.7 | 9.3 |
| 2.5 | 5.8 |

The powder x-ray diffraction pattern of Form IV is shown in FIG. 4 and values are tabulated in Table IV

TABLE IV

| D-space | I/I$_o$ × 100 |
| --- | --- |
| 12.9 | 43.0 |
| 11.3 | 100.0 |
| 10.5 | 10.3 |
| 9.6 | 6.8 |
| 5.5 | 10.6 |
| 5.1 | 13.7 |
| 4.8 | 4.3 |
| 4.8 | 10.2 |
| 4.6 | 25.6 |
| 4.4 | 5.9 |
| 4.3 | 4.5 |
| 4.2 | 6.6 |
| 4.0 | 23.7 |
| 3.7 | 14.8 |
| 3.7 | 15.4 |
| 3.6 | 7.9 |
| 3.6 | 11.5 |
| 3.5 | 6.5 |
| 3.4 | 15.9 |
| 3.4 | 6.5 |
| 3.4 | 10.1 |
| 3.3 | 8.0 |
| 3.3 | 4.6 |
| 3.1 | 4.1 |
| 2.9 | 5.0 |
| 2.9 | 9.4 |

The powder x-ray diffraction pattern of Form V is shown in FIG. 5 and values are tabulated in Table V.

TABLE V

| D-space | I/I$_o$ × 100 |
| --- | --- |
| 15.0 | 16.3 |
| 13.9 | 56.2 |
| 10.8 | 58.2 |
| 10.1 | 100.0 |
| 7.6 | 23.1 |
| 6.9 | 13.9 |
| 5.7 | 87.7 |
| 5.5 | 45.4 |
| 4.6 | 17.2 |
| 4.5 | 23.4 |
| 4.3 | 28.5 |
| 3.9 | 29.5 |
| 3.8 | 24.7 |
| 3.7 | 17.2 |
| 3.6 | 19.0 |
| 3.6 | 25.5 |
| 3.6 | 22.6 |
| 3.5 | 27.8 |
| 3.4 | 54.9 |
| 3.2 | 27.5 |
| 3.2 | 24.6 |
| 3.1 | 15.3 |
| 3.1 | 16.3 |

The powder x-ray diffraction pattern of Form VI is shown in FIG. 6 and values are tabulated in Table VI.

TABLE VI

| D-space | I/I$_o$ × 100 |
| --- | --- |
| 13.4 | 100.0 |
| 10.9 | 38.4 |
| 10.0 | 23.2 |
| 9.8 | 48.4 |
| 9.0 | 13.9 |
| 8.1 | 14.9 |

TABLE VI-continued

| D-space | I/I$_o$ × 100 |
| --- | --- |
| 7.6 | 23.0 |
| 6.7 | 20.3 |
| 6.2 | 12.6 |
| 5.7 | 40.1 |
| 5.5 | 25.2 |
| 5.4 | 33.1 |
| 5.4 | 37.6 |
| 4.3 | 14.7 |
| 4.2 | 10.0 |
| 4.0 | 11.1 |
| 3.9 | 23.1 |
| 3.8 | 20.3 |
| 3.7 | 17.8 |
| 3.7 | 58.6 |
| 3.6 | 41.8 |
| 3.5 | 16.5 |
| 3.5 | 14.9 |
| 3.4 | 16.2 |
| 3.4 | 19.6 |
| 3.4 | 38.8 |
| 3.2 | 35.4 |
| 3.1 | 15.7 |
| 3.1 | 11.6 |
| 3.0 | 14.4 |
| 3.0 | 16.2 |
| 3.0 | 13.6 |

The powder x-ray diffraction pattern of Form VII is shown in FIG. 7 and values are tabulated in Table VII.

TABLE VII

| D-space | I/I$_o$ × 100 |
| --- | --- |
| 13.9 | 100.0 |
| 10.9 | 15.5 |
| 10.2 | 33.4 |
| 9.3 | 9.4 |
| 7.6 | 11.9 |
| 6.9 | 10.4 |
| 5.7 | 23.8 |
| 5.6 | 33.0 |
| 5.5 | 21.5 |
| 4.4 | 8.9 |
| 4.1 | 8.2 |
| 3.9 | 16.4 |
| 3.8 | 14.4 |
| 3.7 | 14.5 |
| 3.7 | 26.2 |
| 3.5 | 20.8 |
| 3.5 | 9.5 |
| 3.5 | 11.8 |
| 3.4 | 36.7 |
| 3.3 | 27.9 |
| 3.1 | 14.4 |
| 3.1 | 13.2 |
| 2.7 | 10.0 |

The powder x-ray diffraction pattern of Form VIII is shown in FIG. 8*a* and values are tabulated in Table VIII.

TABLE VIII

| D-space | I/I$_o$ × 100 |
| --- | --- |
| 13.0 | 6.6 |
| 12.7 | 8.5 |
| 7.5 | 17.6 |
| 7.2 | 65.6 |
| 6.7 | 34.3 |
| 6.5 | 21.0 |
| 6.1 | 45.3 |
| 4.8 | 6.1 |
| 4.7 | 53.9 |

TABLE VIII-continued

| D-space | I/I$_o$ × 100 |
|---|---|
| 4.4 | 22.1 |
| 4.2 | 14.8 |
| 4.1 | 45.2 |
| 3.9 | 100.0 |
| 3.9 | 19.2 |
| 3.7 | 21.0 |
| 3.6 | 29.4 |
| 3.5 | 11.8 |
| 3.4 | 43.4 |
| 3.3 | 8.3 |
| 3.3 | 25.2 |
| 3.2 | 15.2 |
| 3.2 | 14.0 |
| 3.2 | 14.6 |
| 3.1 | 12.6 |
| 3.1 | 8.3 |
| 3.0 | 14.1 |
| 3.0 | 7.4 |
| 2.8 | 9.4 |
| 2.7 | 6.1 |
| 2.5 | 8.8 |

The powder x-ray diffraction pattern of Form IX is shown in FIG. 9 and values are tabulated in Table IX.

TABLE IX

| D-space | I/I$_o$ × 100 |
|---|---|
| 7.0 | 39.1 |
| 12.3 | 7.0 |
| 13.3 | 58.9 |
| 14.7 | 68.9 |
| 15.2 | 2.6 |
| 16.6 | 3.6 |
| 18.5 | 8.4 |
| 19.1 | 100.0 |
| 20.1 | 23.7 |
| 21.1 | 24.3 |
| 21.9 | 57.7 |
| 22.6 | 35.4 |
| 24.2 | 4.2 |
| 24.8 | 15.1 |
| 25.4 | 19.2 |
| 25.9 | 27.8 |
| 26.7 | 8.7 |
| 26.9 | 32.4 |
| 27.6 | 5.9 |
| 27.9 | 12.9 |
| 28.3 | 21.1 |
| 28.5 | 16.4 |
| 28.7 | 11.0 |
| 28.9 | 10.0 |
| 29.2 | 6.6 |
| 29.6 | 3.3 |
| 30.2 | 5.9 |
| 31.2 | 7.9 |
| 31.8 | 10.9 |
| 32.1 | 3.5 |
| 32.5 | 6.3 |
| 33.5 | 3.5 |
| 34.1 | 5.5 |
| 35.1 | 2.6 |
| 35.6 | 5.4 |
| 36.1 | 8.1 |
| 36.5 | 4.9 |
| 38.0 | 6.2 |

Thermal gravimetric analyses (TGA) were done on Forms II, III, VIII, and IX, as shown in FIGS. 2b, 3b, 8b, and 9b, respectively, and records changes in the mass of a sample as temperature is varied. Physical and chemical stability is shown as measured by DSC thermograms in FIGS. 2b, 3b, 8b, and 9b, respectively.

DEFINITIONS

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined hereinabove" refers to the first definition provided in the Summary of the Invention.

The terms "amorphous state" and "amorphous material" are used herein interchangeably and refer to the compound of Formula Ib in the amorphous state.

The term "optional" or "optionally" as used herein means that a subsequently described event or circumstance may, but need not, occur, and that the description includes instances where the event or circumstance occurs and instances in which it does not. For example, "optionally substituted" means that the moiety may be hydrogen or a substituent.

The term "solvate" as used herein means a compound of the invention or a salt, thereof, that further includes a stoichiometric or non-stoichiometric amount of a solvent bound by non-covalent intermolecular forces. Preferred solvents are volatile, non-toxic, and/or acceptable for administration to humans in trace amounts.

The term "hydrate" as used herein means a compound of the invention or a salt thereof, that further includes a stoichiometric or non-stoichiometric amount of water bound by non-covalent intermolecular forces.

The term "reduced susceptibility" as used herein refers to about a 10 fold, or greater, change in sensitivity of a particular viral isolate compared to the sensitivity exhibited by the wild type virus in the same experimental system.

The term "nucleoside and nucleotide reverse transcriptase inhibitors" ("NRTI"s) as used herein means nucleosides and nucleotides and analogues thereof that inhibit the activity of HIV-1 reverse transcriptase, the enzyme which catalyzes the conversion of viral genomic HIV-1 RNA into proviral HIV-1 DNA.

Typical suitable NRTIs include zidovudine (AZT) available under the RETROVIR tradename; didanosine (ddI) available under the VIDEX tradename.; zalcitabine (ddC) available under the HIVID tradename; stavudine (d4T) available under the ZERIT trademark.; lamivudine (3TC) available under the EPIVIR tradename; abacavir (1592U89) disclosed in WO96/30025 and available under the ZIAGEN trademark; adefovir dipivoxil [bis(POM)-PMEA] available under the PREVON tradename; lobucavir (BMS-180194), a nucleoside reverse transcriptase inhibitor disclosed in EP-0358154 and EP-0736533 and under development by Bristol-Myers Squibb; BCH-10652, a reverse transcriptase inhibitor (in the form of a racemic mixture of BCH-10618 and BCH-10619) under development by Biochem Pharma; emitricitabine [(−)-FTC] licensed from Emory University under U.S. Pat. No. 5,814,639 and under development by Triangle Pharmaceuticals; beta-L-FD4 (also called beta-L-D4C and named beta-L-2',3'-dideoxy-5-fluoro-cytidene) licensed by Yale University to Vion Pharmaceuticals; DAPD, the purine nucleoside, (−)-beta-D-2,6,-diamino-purine dioxolane disclosed in EP-0656778 and licensed to Triangle Pharmaceuticals; and lodenosine (FddA), 9-(2,3-dideoxy-2-fluoro-b-D-threo-pentofuranosyl)adenine, an acid stable purine-based reverse transcriptase inhibitor discovered by the NIH and under development by U.S. Bioscience Inc.

The phrase "immune system modulator or an antiviral compound" as used herein refers to any compound or drug that is useful for treating HIV-1 infections.

The term "non-nucleoside reverse transcriptase inhibitors" ("NNRTI's") as used herein means non-nucleosides that inhibit the activity of HIV-1 reverse transcriptase.

Typical suitable NNRTIs include nevirapine (BI-RG-587) available under the VIRAMUNE tradename; delaviradine (BHAP, U-90152) available under the RESCRIPTOR tradename; efavirenz (DMP-266) a benzoxazin-2-one disclosed in WO94/03440 and available under the SUSTIVA tradename; PNU-142721, a furopyridine-thio-pyrimide; AG-1549 (formerly Shionogi #S-1153); 5-(3,5-dichlorophenyl)-thio-4-isopropyl-1-(4-pyridyl)methyl-1H-imidazol-2-ylmethyl carbonate disclosed in WO 96/10019; MKC-442 (1-(ethoxymethyl)-5-(1-methylethyl)-6-(phenylmethyl)-(2,4(1H,3H)-pyrimidinedione); and (+)-calanolide A (NSC-675451) and B, coumarin derivatives disclosed in U.S. Pat. No. 5,489,697.

The term "protease inhibitor" ("PI") as used herein means inhibitors of the HIV-1 protease, an enzyme required for the proteolytic cleavage of viral polyprotein precursors (e.g., viral GAG and GAG Pol polyproteins), into the individual functional proteins found in infectious HIV-1. HIV protease inhibitors include compounds having a peptidomimetic structure, high molecular weight (7600 daltons) and substantial peptide character, e.g. CRIXIVAN as well as nonpeptide protease inhibitors e.g., VIRACEPT.

Typical suitable PIs include saquinavir available in hard gel capsules under the INVIRASE tradename and as soft gel capsules under the FORTOVASE tradename; ritonavir (ABT-538) available under the NORVIR tradename; indinavir (MK-639) available under the CRIXIVAN tradename; nelfnavir (AG-1343) available under the VIRACEPT; amprenavir (141W94), tradename AGENERASE, a non-peptide protease inhibitor; lasinavir (BMS-234475; originally discovered by Novartis, Basel, Switzerland (CGP-61755); DMP-450, a cyclic urea discovered by Dupont; BMS-2322623, an azapeptide under development by Bristol-Myers Squibb, as a 2nd-generation HIV-1 PI; ABT-378; AG-1549 an orally active imidazole carbamate.

Other antiviral agents include hydroxyurea, ribavirin, IL-2, IL-12, pentafuside and Yissum Project No. 11607. Hydroxyurea (Droxia), a ribonucleoside triphosphate reductase inhibitor, the enzyme involved in the activation of T-cells. Hydroxyurea was shown to have a synergistic effect on the activity of didanosine and has been studied with stavudine. IL-2 is disclosed in Ajinomoto EP-0142268, Takeda EP-0176299, and Chiron U.S. Pat. Nos. RE 33,653, 4,530,787, 4,569,790, 4,604,377, 4,748,234, 4,752,585, and 4,949,314, and is available under the PROLEUKIN (aldesleukin) tradename as a lyophilized powder for IV infusion or sc administration upon reconstitution and dilution with water; a dose of about 1 to about 20 million 1 U/day, sc is preferred; a dose of about 15 million 1 U/day, sc is more preferred. IL-12 is disclosed in WO96/25171 and is available as a dose of about 0.5 microgram/kg/day to about 10 microgram/kg/day, sc is preferred. Pentafuside (DP-178, T-20) a 36-amino acid synthetic peptide, disclosed in U.S. Pat. No. 5,464,933 and available under the FUZEON tradename; pentafuside acts by inhibiting fusion of HIV-1 to target membranes. Pentafuside (3-100 mg/day) is given as a continuous sc infusion or injection together with efavirenz and 2 PI's to HIV-1 positive patients refractory to a triple combination therapy; use of 100 mg/day is preferred. Yissum Project No. 11607, a synthetic protein based on the HIV-1 Vif protein. Ribavirin, 1-.beta.-D-ribofuranosyl-1H-1,2,4-triazole-3-carboxamide, is described in U.S. Pat. No. 4,211,771.

The term "anti-HIV-1 therapy" as used herein means any anti-HIV-1 drug found useful for treating HIV-1 infections in man alone, or as part of multidrug combination therapies, especially the HAART triple and quadruple combination therapies. Typical suitable known anti-HIV-1 therapies include, but are not limited to multidrug combination therapies such as (i) at least three anti-HIV-1 drugs selected from two NRTIs, one PI, a second PI, and one NNRTI; and (ii) at least two anti-HIV-1 drugs selected from NNRTIs and PIs. Typical suitable HAART—multidrug combination therapies include: (a) triple combination therapies such as two NRTIs and one PI; or (b) two NRTIs and one NNRTI; and (c) quadruple combination therapies such as two NRTIs, one PI and a second PI or one NNRTI. In treatment of naive patients, it is preferred to start anti-HIV-1 treatment with the triple combination therapy; the use of two NRTIs and one PI is preferred unless there is intolerance to PIs. Drug compliance is essential. The $CD4^+$ and HIV-1-RNA plasma levels should be monitored every 3-6 months. Should viral load plateau, a fourth drug, e.g., one PI or one NNRTI could be added.

Common abbreviations include: acetyl (Ac), acetic acid (HOAc), azo-bis-isobutyrylnitrile (AIBN), 1-N-hydroxybenzotriazole (HOBT), atmospheres (Atm), high pressure liquid chromatography (HPLC), 9-borabicyclo[3.3.1]nonane (9-BBN or BBN), methyl (Me), tert-butoxycarbonyl (Boc), acetonitrile (MeCN), di-tent-butyl pyrocarbonate or boc anhydride ($BOC_2O$), 1-(3-dimethylaminopropyl)-3-ethyl-carbodiimide hydrochloride (EDCI), benzyl (Bn), m-chloroperbenzoic acid (MCPBA), butyl (Bu), n-butyl acetate (nBuAc), n-butanol (nBuOH), methanol (MeOH), benzyloxycarbonyl (cbz or Z), melting point (mp), carbonyl diimidazole (CDI), $MeSO_2$— (mesyl or Ms), 1,4-diazabicyclo[2.2.2]octane (DABCO), mass spectrum (ms) diethylaminosulfur trifluoride (DAST), methyl t-butyl ether (MTBE), dibenzylideneacetone (Dba), N-carboxyanhydride (NCA), 1,5-diazabicyclo[4.3.0]non-5-ene (DBN), N-bromosuccinimide (NBS), 1,8-diazabicyclo[5.4.0]undec-7-ene (DBU), N-methylpyrrolidone (NMP), 1,2-dichloroethane (DCE), pyridinium chlorochromate (PCC), N,N'-dicyclohexylcarbodiimide (DCC), pyridinium dichromate (PDC), dichloromethane (DCM), propyl (Pr), diethyl azodicarboxylate (DEAD), phenyl (Ph), di-iso-propylazodicarboxylate, DIAD, pounds per square inch (psi), diethyl iso-propylamine (DEIPA), pyridine (pyr), di-iso-butylaluminumhydride, DIBAL-H, room temperature, rt or RT, N,N-dimethyl acetamide (DMA), tert-butyldimethylsilyl or $t$-$BuMe_2Si$, (TB-DMS), 4-N,N-dimethylaminopyridine (DMAP), triethylamine ($Et_3N$ or TEA), N,N-dimethylformamide (DMF), triflate or $CF_3SO_2$— (TO, dimethyl sulfoxide (DMSO), trifluoroacetic acid (TFA), 1,1'-bis-(diphenylphosphino)ethane (dppe), 2,2,6,6-tetramethylheptane-2,6-dione (TMHD), 1,1'-bis-(diphenylphosphino)ferrocene (dppf), thin layer chromatography (TLC), ethyl acetate (EtOAc), tetrahydrofuran (THF), diethyl ether ($Et_2O$), trimethylsilyl or $Me_3Si$ (TMS), ethyl (Et), p-toluenesulfonic acid monohydrate (TsOH or pTsOH), lithium hexamethyl disilazane (LiHMDS), 4-Me-$C_6H_4SO_2$— or tosyl (Ts), iso-propyl (i-Pr), N-urethane-N-carboxyanhydride (UNCA), ethanol (EtOH). Conventional nomenclature including the prefixes normal (n), iso (i-), secondary (sec-), tertiary (tent-) and neo have their customary meaning when used with an alkyl moiety. (J. Rigaudy and D. P. Klesney, *Nomenclature in Organic Chemistry*, IUPAC 1979 Pergamon Press, Oxford.).

EXAMPLES

Examples of representative polymorphs encompassed by the present invention and within the scope of the invention are described in the examples below. The polymorphs described in the preparative examples which follow are provided to enable those skilled in the art to more clearly understand and to practice the present invention. They should not be considered as limiting the scope of the invention, but merely as being illustrative and representative thereof.

In general, the nomenclature used in this Application is based on AUTONOM™ v. 4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

Salts and polymorphs of the present invention are made by a variety of methods depicted in the illustrative synthetic reaction schemes shown and described below. Compound I

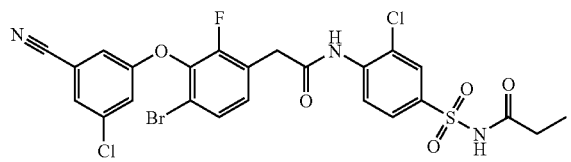

I was prepared according to U.S. Pat. No. 7,166,738, which is hereby incorporated by reference in its entirety.

The starting materials and reagents used in preparing these salts and polymorphs thereof generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, Volumes 1-21; R. C. LaRock, *Comprehensive Organic Transformations*, 2nd edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 1-40.

Formulations and Administration

Formulations of compounds of formula I may be prepared by processes known in the formulation art. The following examples (infra) are given to enable those skilled in the art to more clearly understand and to practice the present invention. They should not be considered as limiting the scope of the invention, but merely as being illustrative and representative thereof.

The polymorphic salts of the present invention can be administered in a variety of oral and parenteral dosage forms. Oral dosage forms can be tablets, coated tablets, dragées, hard and soft gelatin capsules, solutions, emulsions, syrups, or suspensions. Parenteral administration includes intravenous, intramuscular, intracutaneous, subcutaneous, intraduodenal, or intraperitoneal administration. Additionally, the salts of the present invention can be administered by transdermal (which may include a penetration enhancement agent), buccal, nasal and suppository routes. Also, the salts can be administered by inhalation.

The compounds of the present invention may be formulated in a wide variety of oral administration dosage forms and carriers. Oral administration can be in the form of tablets, coated tablets, dragées, hard and soft gelatine capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The term "excipient" as used herein includes both one and more than one such excipient.

The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. N-acylsulfonamides have an acidic proton which can be abstracted to form a salt with an organic or inorganic cation.

The preferred pharmaceutically acceptable salts are the salts formed from acetic acid, hydrochloric acid, sulphuric acid, methanesulfonic acid, maleic acid, phosphoric acid, tartaric acid, citric acid, sodium, potassium, calcium, zinc, and magnesium. It should be understood that all references to pharmaceutically acceptable salts include solvent addition forms (solvates) or crystal forms (polymorphs) as defined herein, of the same acid addition salt.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to a skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polyactic acid.

Suitable formulations along with pharmaceutical carriers, diluents and expcipients are described in Remington: The Science and Practice of Pharmacy 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 100 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

In embodiments of the invention, the active compound or a salt can be administered in combination with another antiviral agent, such as a nucleoside reverse transcriptase inhibitor, another nonnucleoside reverse transcriptase inhibitor or HIV protease inhibitor. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

It will be understood that references herein to treatment extend to prophylaxis as well as to the treatment of existing conditions, and that the treatment of animals includes the treatment of humans as well as other animals. Furthermore, treatment of a HIV infection, as used herein, also includes treatment or prophylaxis of a disease or a condition associated with or mediated by HIV infection, or the clinical symptoms thereof.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Preparation of Polymorphic Forms

Example 1

Na salt of compound I, 2-[4-Bromo-3-(3-chloro-5-cyano-phenoxy)-2-fluoro-phenyl]-N-(2-chloro-4-propionylsulfamoyl-phenyl)-acetamide, sodium salt
(Ib)

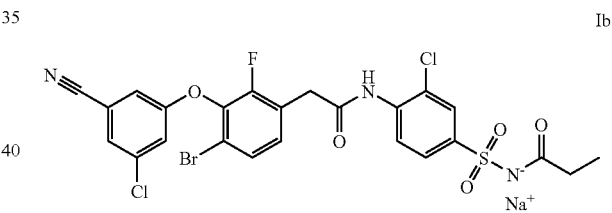

81 g Compound I in 800 mL THF was heated to reflux, 1 L toluene added and 500 mL solvent distilled out, and 1.2 L toluene added and solvent distilled out to remove a total of 2 L, to yield crystalline product that was filtered, rinsed with toluene, and solvent removed in vacuo to yield crystalline compound I. 40.6 g of crystalline compound I from Example 1 was then dissolved in 600 mL THF and 60 mL 1M NaOH, then 500 mL H₂O, and additional 1M NaOH added to bring the pH to 8.05.

Example 2

Na Salt of Compound I (Ib)

Compound I was recrystallized from MeOH. 24 g compound I recrystallized from MeOH was dissolved in 80 mL THF and 20 mL 1M NaOH was added and then diluted with 60 mL H₂O and 1M NaOH added until a pH of 8 was reached. The solution was filtered, the THF removed in vacuo to form a gel, 200 mL nBuOAc added, and solvent reduced in vacuo to form a thick gel. 10 mL THF added to form a semi-solution and heated to 60° C. in vacuo until crystals started forming then heated to 80° C. in vacuo, let cool, 100 mL nBuOAc added, and the product filtered off, washed with nBuOAc, and solvent removed in vacuo with heating to yield 21.6 g sodium salt of compound I.

Example 3

Polymorph II of Na Salt of Compound I (Ib)

284.4 g compound I dissolved in 2 L distilled THF in a 5 L flask and pH adjusted to 7.98 with 1M NaOH slowly added with the addition of 2 L $H_2O$. The solution was then heated to 46° C. and the THF removed in vacuo and the solution filtered and 2 L $H_2O$ added and filtered again and cooled to 4° C. to yield a first suspension. 20.9 g sodium salt of compound I from Example 1 and 21.6 g sodium salt of compound I from Example 2 were both added to the first suspension with 4 L THF to generate a homogenous solution which was then filtered. The bulk of the THF was then removed in vacuo and 3 L pre-filtered nBuOH added and the solvent reduced by 5 L in vacuo at 55° C. 1 L pre-filtered nBuOAc was then added and then reduced to the same volume in vacuo. 3 L pre-filtered nBuOAc was then added, the solution heated to 80° C., the solvent reduced by 1 L in vacuo, the solution cooled to 60° C., 1 L pre-filtered nBuOAc was then added. The solution was then heated to 82° C. to yield crystalline product that was then filtered off and washed with nBuOAc and solvent removed in vacuo at 70° C. for 1 day, 80° C. for 1 day, and 90° C. for 3 days to yield 307 g product.

Example 4

Na Salt of Compound I (Ib)

250 g compound I recrystallized from MeOH was dissolved in 1.5 L THF and 250 mL 1M NaOH in $H_2O$ added followed by 1 L $H_2O$. 150 mL 1M NaOH in $H_2O$ added to bring the solution to pH 8.00. The mixture was then filtered the concentrated in vacuo until $H_2O$ started to distill. nBuOH was then added and the solution again concentrated in vacuo until the $H_2O$ stopped distilling. nBuOAc was then added and the solvent concentrated in vacuo, and addition and removal repeated until solution became cloudy at 60° C. The mixture was then agitated overnight and resulted in crystals which were filtered off and rinsed with nBuOAc and dried in vacuo at 80° C. and then 100° C. to yield 205 g Na salt of compound I (Ib).

Example 5

Crystal Forms for the Na Salt of Compound I

Form I: (Undried Sample):
  Form I (hydrate/solvate) can be prepared by recrystallization from THF/water/n-butanol/n-butylacetate solvent system.
Form II:
  Form II (hydrate/solvate) can be prepared by heating/drying Form I. It can also be formed by suspending Form III in MeOH.
Form III:
  Form III (anhydrous) can be prepared by recrystallization in THF/water/n-butanol/n-butyl acetate solvent system or THF/nBuAc. It can also be prepared by suspending Form II or Form IV in butanone. Suspending Form II in methyl isobutyl ketone will also make Form III.

Form IV:
  Form IV (hydrate/solvate) can be prepared by suspending Form II in pentanol.
Form V:
  Form V (hydrate/solvate) can be prepared by suspending Form II in THF.
Form VI:
  Form VI (hydrate/solvate) can be prepared by suspending Form II in ethanol, isopropanol, 70% IPA/30% $H_2O$, isopropyl acetate, acetone, or heptane. Form VI can also be prepared suspending Form III in 70% IPA/30% $H_2O$.
Form VII:
  Form VII (hydrate/solvate) can be prepared by suspending Form II in pentane.
Form VIII:
  Form VIII (anhydrous) can be prepared by recrystallization in THF/water/butyl acetate. It can also be prepared by suspending Form III in acetonitrile, isopropanol/water and acetonitrile/water solvent systems. Suspending Form II in acetonitrile can also produce Form VIII.
Form IX:
  Form IX (anhydrous) can be prepared by suspending Form VIII in acetonitrile at elevated temperatures.
Amorphous Material:
  Amorphous state of Ib can be prepared by dissolving Form VIII in 82% t-butanol/18% water at a drug concentration of ~6 mg/mL. This solution was lyophilized overnight (~18 hours) to form the amorphous material. The amorphous material is stable at 25C/60 RH for at least one week but not at 40C/75 RH.

Example 6

The Interconversion Scheme of Crystalline Polymorph Forms I-IX and Amorphous State of Ib is Detailed in FIG. 13

Example 7

Scale-Up Procedure 4.5 kg of the Na salt Form III was dissolved in THF about 45 L, and treated at ambient temperature with HCl to a pH of 1. The mixture was polish filtered to clarify, and the free acid was crystallized by replacing the THF with toluene at a constant volume, with atmospheric distillation to a pot temperature of 108° C. The mixture was cooled, and the solid was filtered. The wet cake was dissolved in a mixture of about 6 kg DMF, 20 kg IPA. About 4 L of this solvent mixture was capable of dissolving about 1 kg of substrate at 80° C. Once full solution was achieved, water (about 9 kg) was added slowly while maintaining temperature. The free acid crystallized from this mixture upon cooling to 10° C. and was filtered and washed with IPA, then transferred to a vacuum oven and dried.

The salt was then reformed by dissolving the fee acid in THF (about 5-10 L per kg) and treating with 2 equivalents Na-2-ethyl-hexanoate (a soluble sodium salt). This solution was filtered, and then the THF replaced by atmospheric distillation by Butyl acetate to a pot temperature of 127° C. to induce crystallization. Once this pot temperature was achieved, the vessel was sealed and heated to 135° C. for about 45 min. The mixture was cooled to ambient temperature and filtered, washed with butyl acetate and dried in a vacuum oven. PXRD for this material (form VIII) did not match our previous batch of form III.

Example 8

Method for Recrystallization of Form VIII of the Na Salt of Compound I 100 grams of Na salt of compound I were dissolved in 100 mL water and 100 mL isopropanol mixture at reflux. Then seeding the hot solution with form VIII, diluting with IPA (3.75 L), cooling and filtering at 5° C. gave about 90% yield of recrystallized form VIII at purity of about 99% by AN HPLC.

Example 9

X-Ray Powder Pattern

The X-ray powder diffraction patterns of samples of the polymorphic crystals were measured on a Scintag X1 powder X-ray diffractometer equipped with a sealed copper $K\alpha_1$ irradiation source. The samples were scanned from 2° to 40° 2θ at a rate of 3° per minute with incident beam slit widths of 4 and 2 microns and diffracted beam slit widths of 0.5 and 0.2 microns.

Example 10

Thermochemical Analyses

DSC Thermograms were collected using a 2920 Modulated DSC from Thermal Analyzer (TA) Instruments. The heating rate was 10° C./min with a nitrogen purge maintained throughout the run.

Thermogravimetric (TGA) analysis was conducted using a Hi-Res 2950 TGA (TA Instruments). The sample was heated from 30° C.-280° C. at a rate of 10° C./min and a nitrogen flow was maintained throughout each run.

Example 11

Pharmaceutical Compositions

Pharmaceutical compositions of the subject Compounds for administration via several routes can be prepared as described in this Example.

| Composition for Oral Administration (A) | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration (B) | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration (C) | |
|---|---|
| Ingredient | % wt./wt. |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation (D) | |
|---|---|
| Ingredient | % wt./wt. |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation (E) | |
|---|---|
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

| Topical Formulation (F) | |
|---|---|
| Ingredients | grams |
| Active compound | 0.2-2 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. 100 |

All of the ingredients, except water, are combined and heated to about 60° C. with stirring. A sufficient quantity of water at about 60° C. is then added with vigorous stirring to emulsify the ingredients, and water then added q.s. about 100 g.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. A polymorphic crystalline form (Form I) of the compound

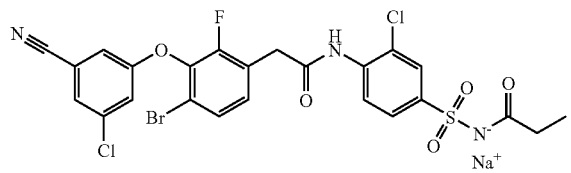

Ib according to formula Ib with an x-ray powder diffraction trace having a D-spacing as shown:

| D-space | $I/I_o \times 100$ |
| --- | --- |
| 15.1 | 100.0 |
| 10.9 | 21.9 |
| 6.0 | 39.5 |
| 3.2 | 30.0. |

2. A polymorphic crystalline form (Form II) of the compound

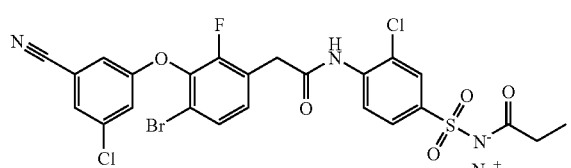

Ib according to formula Ib with an x-ray powder diffraction trace having a D-spacing as shown:

| D-space | $I/I_o \times 100$ |
| --- | --- |
| 13.2 | 100.0 |
| 9.8 | 44.0 |
| 7.9 | 20.9 |
| 7.6 | 17.3 |
| 5.3 | 30.5. |

3. A polymorphic crystalline form (Form III) of the compound

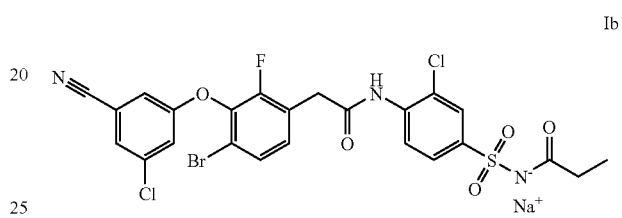

Ib according to formula Ib with an x-ray powder diffraction trace having a D-spacing as shown:

| D-space | $I/I_o \times 100$ |
| --- | --- |
| 6.8 | 100.0 |
| 4.6 | 44.0 |
| 4.4 | 31.7 |
| 4.1 | 31.5 |
| 3.7 | 36.9 |
| 3.6 | 42.7 |
| 3.4 | 32.3. |

4. A polymorphic crystalline form (Form IV) of the compound

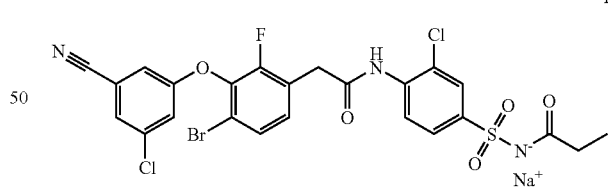

Ib according to formula Ib with an x-ray powder diffraction trace having a D-spacing as shown:

| D-space | $I/I_o \times 100$ |
| --- | --- |
| 12.9 | 43.0 |
| 11.3 | 100.0 |
| 4.6 | 25.6 |
| 4.0 | 23.7. |

5. A polymorphic crystalline form (Form V) of the compound

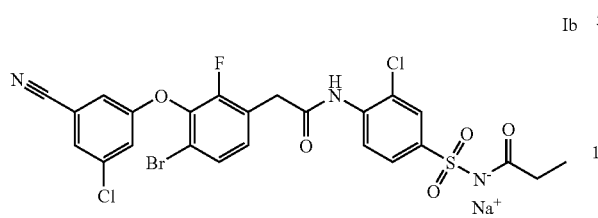

according to formula Ib with an x-ray powder diffraction trace having a D-spacing as shown:

| D-space | I/I$_o$ × 100 |
|---------|---------------|
| 13.9 | 56.2 |
| 10.8 | 58.2 |
| 10.1 | 100 |
| 5.7 | 87.7 |
| 5.5 | 45.4 |
| 3.4 | 54.9 |
| 3.2 | 27.5. |

6. A polymorphic crystalline form (Form VI) of the compound

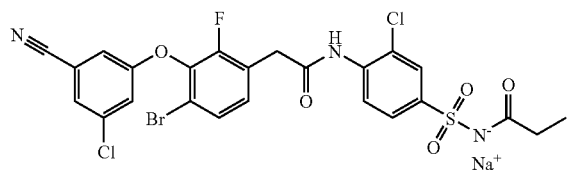

according to formula Ib with an x-ray powder diffraction trace having a D-spacing as shown:

| D-space | I/I$_o$ × 100 |
|---------|---------------|
| 13.4 | 100.0 |
| 10.9 | 38.4 |
| 9.8 | 48.4 |
| 5.7 | 40.1 |
| 5.4 | 37.6 |
| 3.6 | 41.8 |
| 3.4 | 38.8 |
| 3.2 | 35.4. |

7. A polymorphic crystalline form (Form VII) of the compound

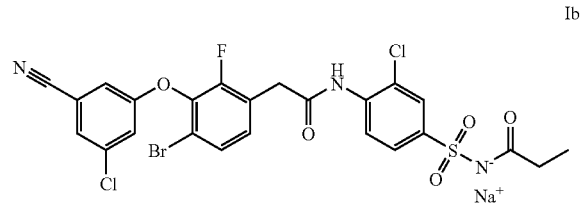

according to formula Ib with an x-ray powder diffraction trace having a D-spacing as shown:

| D-space | I/I$_o$ × 100 |
|---------|---------------|
| 13.9 | 100.0 |
| 10.2 | 33.4 |
| 5.6 | 33.0 |
| 3.7 | 26.2 |
| 3.4 | 36.7 |
| 3.3 | 27.9. |

8. A polymorphic crystalline form (Form VIII) of the compound according to formula Ib with an x-ray powder diffraction trace having a D-spacing as shown:

| D-space | I/I$_o$ × 100 |
|---------|---------------|
| 7.2 | 65.6 |
| 6.7 | 34.3 |
| 6.1 | 45.3 |
| 4.7 | 53.9 |
| 4.1 | 45.2 |
| 3.9 | 100.0 |
| 3.4 | 43.4. |

9. A polymorphic crystalline form (Form IX) of the compound

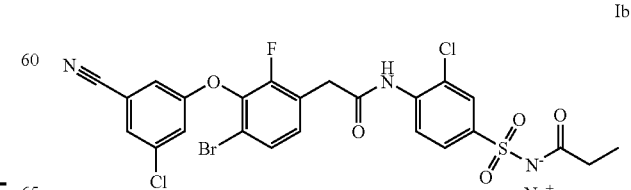

according to formula Ib with an x-ray powder diffraction trace having a D-spacing as shown:

| D-space | I/I$_o$ × 100 |
|---|---|
| 12.6 | 39.1 |
| 6.6 | 58.9 |
| 6.0 | 68.9 |
| 4.6 | 100.0 |
| 4.0 | 57.7 |
| 3.9 | 35.4 |
| 3.3 | 32.4. |

10. A process for preparing the polymorphic crystalline form (Form III) of claim 3 comprising crystallizing the compound (Ib) from THF/water/n-butanol/n-butyl acetate, THF/nBuAc, butanone, or methyl isobutyl ketone.

11. A process for preparing the polymorphic crystalline form (Form VIII) of claim 8 comprising crystallizing the compound (Ib) from THF/water/butyl acetate, acetonitrile, acetonitrile/water, or isopropanol/water.

12. A process for preparing the polymorphic crystalline form (Form IX) of claim 9 comprising crystallizing the compound (Ib) from acetonitrile.

13. A pharmaceutical composition comprising the crystalline form of claim 9, in admixture with at least one pharmaceutically acceptable carrier, diluent or excipient.

14. A pharmaceutical composition comprising an amorphous state of the compound

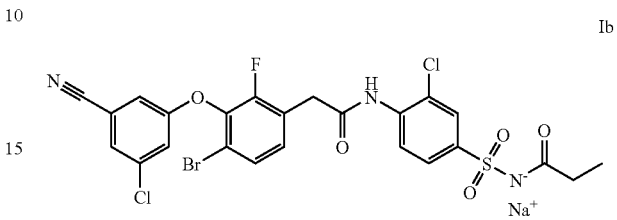

according to formula Ib characterized by the X-ray powder diffraction pattern in FIG. 10 in admixture with at least one pharmaceutically acceptable carrier, diluent or excipient.

* * * * *